US00PP12467P2

(12) United States Plant Patent
Cosner et al.

(10) Patent No.: US PP12,467 P2
(45) Date of Patent: Mar. 19, 2002

(54) IMPATIENS PLANT NAMED 'TIROW'

(76) Inventors: Harlan B. Cosner; Susan L. Cosner, both of P.O. Box 173, Broadbent, OR (US) 97414

( * ) Notice: Subject to any disclaimer, the term of this patent is extended or adjusted under 35 U.S.C. 154(b) by 0 days.

(21) Appl. No.: 09/534,642

(22) Filed: Mar. 23, 2000

(30) Foreign Application Priority Data

Mar. 30, 1999 (CA) ..... 99-1614

(51) Int. Cl.[7] ..... A01H 5/00
(52) U.S. Cl. ..... Plt./317
(58) Field of Search ..... Plt./317, 319

(56) References Cited

PUBLICATIONS

UPOV–ROM GTITM Computer Database, 2000/06, GTI Jouve Retrieval Software, citation for 'TiRow'.*

* cited by examiner

*Primary Examiner*—Bruce R. Campell
*Assistant Examiner*—Susan B. McCormick
(74) *Attorney, Agent, or Firm*—Bradley M. Ganz, Esq.

(57) ABSTRACT

A new and distinct cultivar of *Impatiens walleriana* plant named 'TiRow' characterized by large pink bi-colored fully double flowers, flowers that are positioned above or beyond the foliage, good heat tolerance, dark green foliage and mounded, freely branching and dense plant habit.

1 Drawing Sheet

BACKGROUND—FIELD OF INVENTION

The present invention relates to a new and distinct cultivar botanically known as *Impatiens walleriana*, and by the cultivar name 'TiRow'.

The cultivar of the photograph was developed and selected in a controlled breeding program in a controlled environment in Broadbent, Oreg. by the inventors, Harlan Cosner and Sue Cosner, as described herein.

BACKGROUND—DESCRIPTION OF THE PRIOR ART

The closest known cultivar of prior art is named 'Sparkler Rose', subject of U.S. Plant Pat. No. 9,603.

COMPARISON

The impatiens plant of the present invention differs from prior plants, namely 'Sparkler Rose' in at least the following ways:

1. The plant of the present invention has been shown to perform better in the heat than 'Sparkler Rose';

2. The flowers of the present invention are much larger, generally a full centimeter, than the flowers of 'Sparkler Rose';

3. The flower colors of 'Sparkler Rose' tend to bleed into each other while the flower colors of the present invention have a clear division between the pink and the whitish colors; and 4. The foliage of the present invention is darker green than the foliage of 'Sparkler Rose'.

These and other characteristics will be apparent to persons skilled in the art.

BACKGROUND—DISCOVERY

The present cultivar was developed by standard cross-pollination. Its seed parent is a semi-double impatiens plant with large hot pink flowers. This plant was designated B-9X-1377 under the inventors' controlled breeding program. The pollen parent is a pollen-producing double impatiens plant with purple and white bi-colored flowers. This plant was designated B-9X-237 under the inventors' controlled breeding program. The parent plants are not the subject of any granted patent or pending application. The cross was made in the inventors' controlled breeding program, and the first asexual reproduction was made at Broadbent, Oreg. Successive asexually reproduced generations have shown the present invention to be stable. Each asexually reproduced generation has been accomplished using lateral stems with leaves.

The traits of the cultivar of the present invention that have been observed in each successive generation of asexual reproduction, and which are unique, are the large pink bi-colored fully double flowers, flowers that are positioned above or beyond the foliage, good heat tolerance, dark green foliage and mounded, freely branching and dense plant habit and both male and female sterility.

Color references are according to The Royal Horticultural Society Colour Chart, except where general terms of ordinary dictionary significance are used.

DETAILED DESCRIPTION

The following observations, measurements and description of the plants and flowers are based on the environmental and cultural practices at Broadbent, Oreg. The following measurements, values and comparisons describe plants grown under a double layer of polyethylene film with temperatures typically ranging from about 55° F. to about 85° F. during the daytime. Night heat was provided by bench top set at 62° F. The individual plants were grown in six-inch Azalea containers in a soiless medium. Plants were liquid fed with high nitrate plus trace elements applied at N level 150 PPM of two successive feedings followed by one leaching with clear water. Plants started in the last week of June and finished in late September. Light levels were between 4,000 and 6,000 ft. candles.

The plant of the present invention has not been observed in all possible environmental and/or cultural conditions. The phenotype may vary significantly with variations in environment such as temperature, light level, humidity and also with cultural practices such as fertility, soil and water quality.

The accompanying photograph illustrates the overall appearance and the flower color of the cultivar of the present invention described herein. The photograph was taken of a mature plant 14 weeks of age and during full inflorescence. There may be variations between the colors in the photograph and the colors in the following description due to, for example, light reflectance, or the amount of blue or red light captured in the film. If such variations occur, the written description shall control.

Parentage: The new cultivar was developed by standard cross-pollination. As noted above, its seed parent was a semi-double with large hot pink flowers; its pollen parent was a pollen-producing double with purple and white bi-colored flowers.

Propagation:

*Type cutting.*—Lateral stems with leaves were the cuttings used for asexual reproduction.

*Time to initiate roots.*—Approximately 7 to 14 days at 72° F. soil temperature.

Appearance and form of plant:

*Plant form and habit.*—Mounded to prostate mounded, with a medium vigorous, dense and bushy growing habit. A free-branching habit.

*Plant size.*—Height is about 20 cm, and width is about 30 cm.

*Root description.*—Numerous, fibrous and well-branched roots characterize the rooting habit.

*Branching habit.*—Plants are self-branching. Stems are strong and freely produced. The number of stems depends upon cultural practices, age of stems used as cuttings and the number of growth buds present on the cutting when stuck. The observed plant's average stem length is about 15 cm. Each stem generally produces about three laterals.

*Stems.*—Length of stems varies with age and cultural practices. Diameter is about 0.5 cm, internode length is about 2.5 cm. Color is 144A on newer growth, developing dark spots or streaks with age, the color of which is hard to determine due to their small size, but which appear close to either 176A or 178A, these spots or streaks appear in the greatest numbers at the node regions. The observed plant's stem texture is smooth.

*Foliage.*—Leaves are simple, generally symmetrical, abundant, alternate and flat. Shape is ovate to elliptic, with acuminate apex, attenuate base, and crenate margin. The texture is satiny and smooth. The observed plant's leaf venation pattern is similar to other plants having similar leaf shapes, with single veins branching upwardly off from the central, longitudinal axis, along the length of the axis, toward the margin of the leaf and forming an acute angle relative to the axis.

*Foliage size.*—Size of the largest leaves is about 6.5 cm in length, and 4.5 cm in width.

*Foliage color.*—Adaxial surface color is darker than 147A venation is 146A. Abaxial surface is 147B with dark markings that appear closest to 187A with a greenish overtone that makes them hard to determine with precision, venation is 146A.

*Petioles.*—Each petiole is half round with a flat upper surface. The largest have a width of about 2.5 mm, a depth of about 2 mm, and a length of about 3 cm. Adaxial surface color is close to 148B toward base, darkening to 148A at leaf end. Small reddish streaks may appear with age, and due to their small size, their color is hard to determine, but appears close to 176A. Abaxial surface is close to 147C at base, changing to 147B toward leaf end.

*Flower size.*—The largest flowers have a diameter of about 5.5 cm a depth of about 2.5 cm and a petal count of 30 or more.

*Flower texture.*—The flower texture is smooth and satiny.

*Flower count.*—12 to 15 flowers per branch at any time during the flowering season (count includes visible buds to mature, fully open flowers).

*Flower fragrance.*—No discernible fragrance.

*Natural flowering season.*—Year around under greenhouse conditions and the frost-free period from spring through fall outdoors.

*Duration of flowering.*—Continous throughout the flowering season.

*Time to flower.*—About six weeks from a rooted cutting.

*Buds.*—Buds are ovate in shape with a length of about 1.3 cm, a width of about 0.8 cm and a depth of about 1 cm. Tops of the buds are closest to 145A with small markings appearing close to 67D. Bottoms of buds are 145D.

*Petal size and shape.*—Largest petals consist of two fused at the base. Length is about 3 cm and width is about 2 cm. Shape is exaggerated obovate (closer to the reverse of deltoid), cuneate to obtuse base, entire margin, obtuse to refuse apex.

*Petal color.*—Adaxial surface is generally variegated with 66A and a light color (not matching any in the chart) lighter than 76D or 69D. Abaxial surface is generally variegated with 66D and a light color (not matching any color in the chart) lighter than 76D or 69D.

*Petal count.*—Numerous, generally 30 or more.

*Spur.*—Shape is a curved acicular tube about 4 cm in length. Width at sepal end is about 2 mm. Color is 144B with a dark apex spot too small to determine but appears close to 187B. There are also tiny markings toward the base that appear close to 187D.

*Calyx.*—The calyx consists of a single sepal. The sepal has a length of about 1.5 cm and a width of about 1.2 cm. Color of adaxial surface is 142D with a darker apex appearing close to 143B, a basal circle at point of spur attachment close to 63A, a picotee type of ring appearing close to 69D to 76D with small markings close to 63A (this ring extends from base to apex on each side). Abaxial surface color is 145C to 145D with a darker apex close to 144A, with a picotee type of edge of 69D to 76D extending from base to apex with small markings close to 66A within this picotee type of edge. Shape is elliptic with entire margin, cordate base, cuspidate apex.

*Peduncles.*—Length is about 2.7 cm and diameter is about 3 mm. Color is between 146B and 146C, but closer to 146B. Peduncles have a smooth texture.

*Pedicels.*—Usually two or three. Length is about 2.7 cm and diameter is about 1.7 mm. Color is between 146B and 146C but closer to 146B with a reddish tinge. Pedicels have a smooth texture.

*Reproductive organs.*—The plants of the new cultivar are both male and female sterile. No reproductive organs have been found to exist.

*Disease resistance.*—The instant plant has shown good resistance to botrytis.

*Rooting ability.*—Easy, no hormones are needed.

*Cold/heat resistance.*—Plants of the present invention and 'Sparkler Rose' were grown side by side under shade cloth at Alva, Fla. during late spring through July. The day temperature was in the mid 90° F. range. 'Sparkler Rose' remained small and lacked vigor or strength, the flower color appeared smoky, while 'TiRow' grew strong, had large flowers and the colors were clear and bright.

*Dampness resistance.*—Outdoors during rainy weather at Broadbent, Oreg., 'Sparkler Rose' showed weakness in its peduncles and pedicels which caused the flowers to droop or face down during rains. Even after rains, the flowers of 'Sparkler Rose' that drooped during rains remained drooped or face down until they were shed. In comparison, the flowers of 'TiRow' remained face up or out and seldom drooped during rainy weather.

What is claimed:

1. A new and distinct cultivar of *Impatiens walleriana* as illustrated and as described herein.

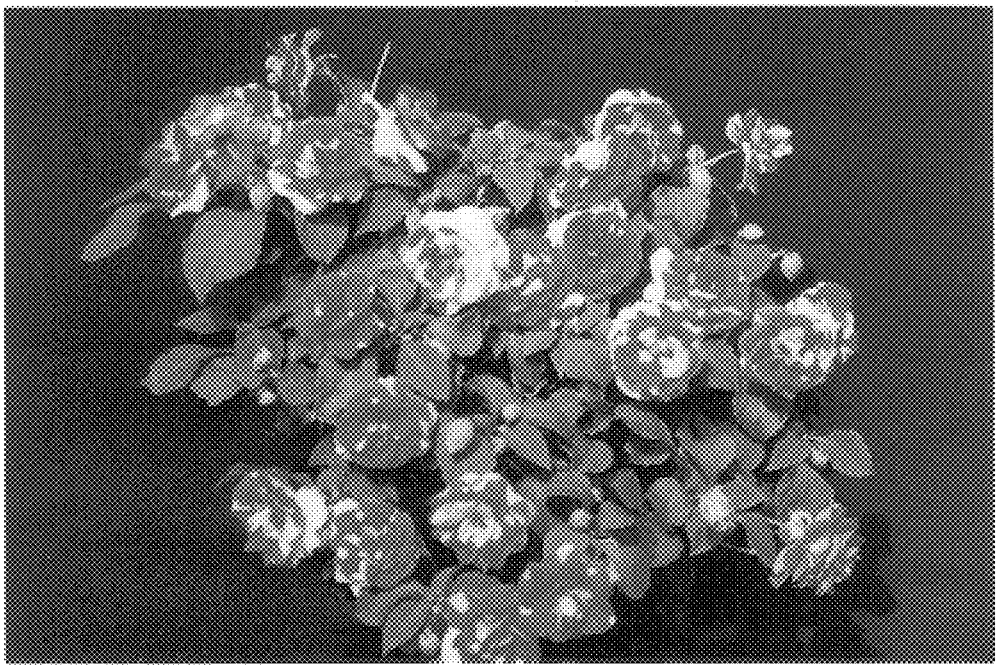

* * * * *